United States Patent
Halff et al.

(10) Patent No.: US 8,803,688 B2
(45) Date of Patent: Aug. 12, 2014

(54) SYSTEM AND METHOD RESPONSIVE TO AN EVENT DETECTED AT A GLUCOSE MONITORING DEVICE

(75) Inventors: Lisa Halff, San Antonio, TX (US); Hami Halff, San Antonio, TX (US); Nicole Y Sunaryo, Austin, TX (US); Huda Abdul-Razzak, Houston, TX (US); Scott Aron Tarver, Chicago, IL (US); Michael Yim, Lubbock, TX (US)

(73) Assignees: Lisa Halff, San Antonio, TX (US); Larry Halff, San Antonio, TX (US)

( * ) Notice: Subject to any disclaimer, the term of this patent is extended or adjusted under 35 U.S.C. 154(b) by 490 days.

(21) Appl. No.: 12/763,472

(22) Filed: Apr. 20, 2010

(65) Prior Publication Data
US 2011/0163881 A1    Jul. 7, 2011

Related U.S. Application Data
(63) Continuation-in-part of application No. 12/683,626, filed on Jan. 7, 2010.

(51) Int. Cl.
G08B 21/00 (2006.01)
(52) U.S. Cl.
USPC ............. 340/573.1; 340/539.15; 340/539.23; 600/301; 600/365; 604/890.1; 604/66; 434/236
(58) Field of Classification Search
USPC ..................... 340/573.1; 434/236; 600/365; 604/890.1, 66
See application file for complete search history.

(56) References Cited

U.S. PATENT DOCUMENTS

| | | | |
|---|---|---|---|
| 5,593,852 A | 1/1997 | Heller et al. | |
| 5,960,403 A * | 9/1999 | Brown | 705/2 |
| 6,475,750 B1 | 11/2002 | Han et al. | |
| 6,572,542 B1 * | 6/2003 | Houben et al. | 600/300 |
| 6,650,951 B1 | 11/2003 | Jones et al. | |
| 6,727,814 B2 * | 4/2004 | Saltzstein et al. | 340/531 |
| 6,744,350 B2 | 6/2004 | Blomquist | |
| 6,852,104 B2 | 2/2005 | Blomquist | |
| 7,294,107 B2 * | 11/2007 | Simon et al. | 600/300 |
| 2002/0126036 A1 | 9/2002 | Flaherty et al. | |
| 2002/0158775 A1 * | 10/2002 | Wallace | 340/870.07 |
| 2003/0163088 A1 | 8/2003 | Blomquist | |
| 2003/0208113 A1 | 11/2003 | Mault et al. | |
| 2003/0212317 A1 | 11/2003 | Kovatchev et al. | |
| 2003/0212364 A1 | 11/2003 | Mann et al. | |
| 2003/0212379 A1 | 11/2003 | Bylund et al. | |
| 2003/0213489 A1 * | 11/2003 | Mechlenburg et al. | 128/204.18 |
| 2005/0143864 A1 | 6/2005 | Blomquist | |
| 2006/0001538 A1 | 1/2006 | Kraft et al. | |
| 2006/0001551 A1 | 1/2006 | Kraft et al. | |
| 2006/0132292 A1 | 6/2006 | Blomquist | |
| 2006/0135907 A1 | 6/2006 | Remde et al. | |
| 2006/0290496 A1 | 12/2006 | Peeters | |

(Continued)

FOREIGN PATENT DOCUMENTS
WO    WO0152014 A2    7/2001

*Primary Examiner* — Nabil Syed
*Assistant Examiner* — Mark Rushing
(74) *Attorney, Agent, or Firm* — Christopher & Weisberg, P.A.

(57) ABSTRACT

Embodiments include an apparatus responsive to an event detected at a glucose monitoring device. The apparatus includes circuitry to select an action to occur remote to the glucose monitoring device in response to the event. Embodiments include a response center responsive to an event at a glucose monitoring device to contact a person in response to the event.

16 Claims, 12 Drawing Sheets

(56) References Cited

U.S. PATENT DOCUMENTS

| | | |
|---|---|---|
| 2007/0219480 A1 | 9/2007 | Kamen |
| 2008/0119705 A1 | 5/2008 | Patel |
| 2008/0125701 A1 | 5/2008 | Moberg et al. |
| 2008/0139910 A1 | 6/2008 | Mastrototaro et al. |
| 2008/0318624 A1 | 12/2008 | Hedtke et al. |
| 2009/0005729 A1 | 1/2009 | Hendrixson et al. |
| 2009/0069784 A1 | 3/2009 | Estes et al. |
| 2009/0177142 A1 | 7/2009 | Blomquist et al. |
| 2009/0221890 A1 | 9/2009 | Saffer et al. |
| 2009/0275817 A1 | 11/2009 | Feldman et al. |
| 2010/0049025 A1 | 2/2010 | Taub |
| 2010/0163036 A1* | 7/2010 | Hyde et al. ............ 128/203.14 |
| 2010/0331657 A1 | 12/2010 | Mensinger et al. |
| 2011/0006880 A1 | 1/2011 | Long et al. |
| 2011/0050428 A1 | 3/2011 | Istoc |
| 2011/0071464 A1 | 3/2011 | Palerm |
| 2011/0105955 A1 | 5/2011 | Yudovsky et al. |
| 2011/0118578 A1* | 5/2011 | Timmerman ................ 600/365 |
| 2011/0163880 A1 | 7/2011 | Halff et al. |
| 2011/0163881 A1 | 7/2011 | Halff et al. |
| 2011/0205064 A1 | 8/2011 | Strachan et al. |

* cited by examiner

SYSTEM AND METHOD RESPONSIVE TO AN EVENT DETECTED AT A GLUCOSE MONITORING DEVICE

PRIORITY

This application is a continuation-in-part of U.S. patent application Ser. No. 12/683,626, filed on 7 Jan. 2010.

FIELD

This written description is in the field of systems and methods responsive to an event detected at a glucose monitoring device.

BRIEF DESCRIPTION OF THE DRAWINGS

Aspects of embodiments will become apparent upon reading the following detailed description and upon reference to the accompanying drawings in which like references may indicate similar elements.

DETAILED DESCRIPTION

The following is a detailed description of embodiments depicted in the accompanying drawings. The amount of detail offered is not intended to limit the anticipated variations of embodiments; but, on the contrary, the intention is to cover modifications, equivalents, and alternatives falling within the scope of the appended claims. The detailed descriptions below are designed to make such embodiments obvious to a person of ordinary skill in the art.

Embodiments include a method of responding to an event detected at a glucose monitoring device. The method includes selecting a first action to occur remote from the glucose monitoring device in response to the event.

Another embodiment is a method that includes receiving information at a location via a communications network from a unit responsive to an event detected at a glucose monitoring device that is remote from the location. The method includes initiating a contact with at least one person in response to the event.

Another embodiment is an apparatus responsive to an event detected at a glucose monitoring device. The apparatus includes circuitry to select an action to occur remote to the glucose monitoring device in response to the event.

Another embodiment is a response center that includes a memory to store computer instructions and data, and a processor to execute the computer instructions to communicate with a person in response to an event at a glucose monitoring device at a location that is remote from to the response center.

Another embodiment includes a machine-readable medium embodying machine-readable instructions that, when executed by a processor, cause the processor to select an action to occur remote to a glucose monitoring device in response to an event detected at the glucose monitoring device.

Figure 1:
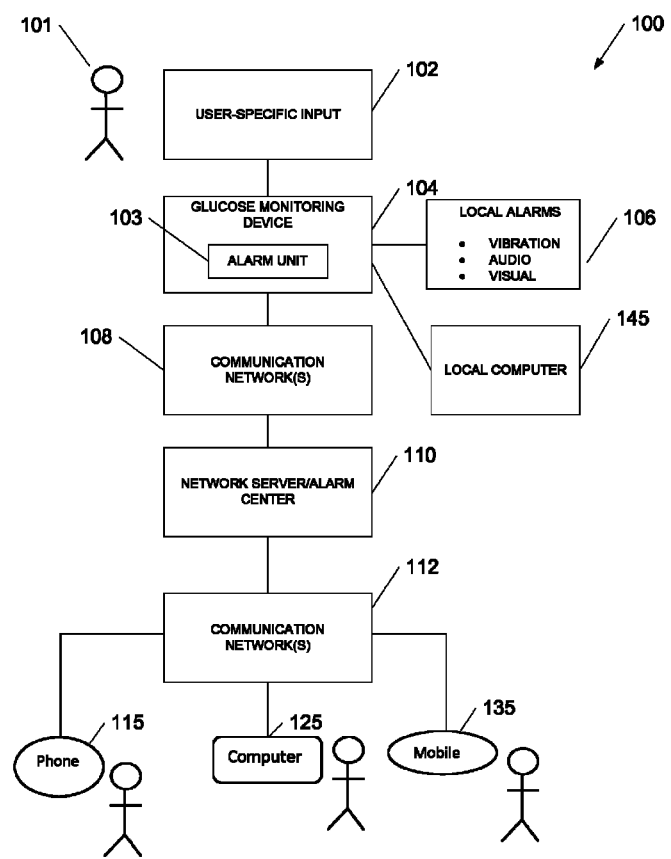
FIG. 1 depicts a first embodiment of a system responsive to an event detected at a glucose monitoring device.

FIG. 1 depicts a first embodiment of a system 100 responsive to an event detected at a glucose monitoring device 104. The glucose monitoring device 104 may be worn in a holster that attaches to a belt of a user 101 of the glucose monitoring device or may be otherwise worn or carried by the user 101. The glucose monitoring device 104 can be actually quite small, on the order of the size of a cell phone. The glucose monitoring device 104 may also deliver insulin through a tube to the user 101, subcutaneously. A steady basal rate of insulin may be supplied in addition to a dose administered at the initiation of the user 101. Other dosing methods may be applied. In other embodiments, the glucose monitoring device does not provide insulin but monitors blood glucose levels. Also, in some embodiments, a remote continuous glucose sensor that the user 101 places under the skin to detect glucose in interstitial tissue may wirelessly transmit the sensed glucose level to the glucose monitoring device 104 so that the glucose monitoring device 104 can detect a low or high blood glucose event, for example.

The glucose monitoring device 104 may receive user specific input 102. For example, the user specific input 102 may include the name, address, phone number, and medical information of the user 101 of the glucose monitoring device 104.

In an illustrative embodiment, the glucose monitoring device 104 may detect an event such as low blood glucose level, high blood glucose level, high glucose rate of change, low power, low memory, or other condition that warrants prompt attention. In some embodiments, the glucose monitoring device 104 may detect high body temperature, high or low blood pressure, or other physiological indication. The glucose monitoring device 104 may respond to an event by vibrating or making a sound. When the user of the glucose monitoring device is awake, he or she can easily feel the relatively weak vibration or hear the relatively low-volume sound generated by the glucose monitoring device 104 when an event occurs. But when the user is asleep, the user may sleep through the warning vibration or sound generated by the glucose monitoring device 104, and possibly lose consciousness, have a seizure, fall into a coma, or even die.

Consequently, the glucose monitoring device 104 may include embedded alarm unit functionality performed by an alarm unit 103, as described herein. The alarm unit functionality is discussed in more detail with reference to FIG. 7. In summary, the alarm unit functionality includes an alarm configuration that enables activation of one or more local alarms 106 and enables communication of alarm information to a communication network 108. The communication network 108 may comprise a plurality of communication networks. In one embodiment, the alarm unit 103 is implemented by application-specific circuitry. In another illustrative embodiment, the alarm unit 103 is implemented by processor circuitry executing computer instructions to cause the processor circuitry to perform alarm unit functions. Thus, in the embodiment of FIG. 1, the alarm unit functionality may be realized using a processor of the glucose monitoring device 104.

The local alarms 106 may include one or more of a strong vibrator, a loud audio alarm, such as a radio or distinctive tone, and a visual alarm. These local alarms are remote (separate) from the glucose monitoring device 104 and may be placed nearby the user 101 or nearby another person. For example, the user 101 may wear the glucose monitoring device 104, place a strong vibrator under his or her pillow when sleeping, and have a loud speaker on a table next to his or her bed. As another example, the loud speaker may be in another room where a significant other, such as a parent or caregiver, may hear it. The vibrator may be a strong vibrator that is substantially stronger than the vibrator of the glucose monitoring device 104. Such vibrators can be positioned under a pillow, and are sometimes used in conjunction with an alarm clock to awaken a deaf person. The vibration of the strong vibrator is strong enough to awaken a person from a sound sleep. Similarly, the loud speaker may emit a loud sound that is loud enough to awaken a person from deep sleep and to notify someone in the vicinity. A visual alarm may include turning on a light, or exhibiting a flashing light, for example, to aid deaf persons.

The local alarms 106 and the communication network 108 may be connected to the glucose monitoring device 104 wirelessly or by wire (including optical fiber). For example, the glucose monitoring device 104 may include a Radio Frequency (RF) transceiver for wireless communications and or a Universal Serial Bus (USB) interface to communicate via a USB cable.

In one embodiment, the glucose monitoring device 104 may detect an event and notify the alarm unit 103. The alarm unit 103 may be configured or programmed to select a first action in response to the detected event. For example, the alarm unit 103 may select to first activate a remote vibrator in response to the detected event. The alarm unit 103 may be configured or programmed to select a second action in response to the detected event if the user 101 of the glucose monitoring device 104 does not respond to the first action. The response required by the alarm unit 103 may include solving a cognitive reasoning skills test. The cognitive reasoning skills test may be selected by the alarm unit at random. For example, the user 101 may be required to solve a simple arithmetic problem within a certain period of time. The second action may include, for example, sending information from the glucose monitoring device 104 to the communications network 108.

The alarm unit 103 may be configured or programmed to select a third action in response to the detected event if the user 101 of the glucose monitoring device 104 does not respond to the second action within a certain period of time. The response required by the alarm unit 103 may include solving a cognitive reasoning skills test. The third action may include, for example, sounding a loud audio alarm. Similarly, a fourth action may be selected if the user 101 does not respond to the third action within a certain period of time, and so forth. Also, multiple actions can be taken simultaneously. For example, a local alarm may be selected to be activated at the same time as information is sent to the communication network 108. As another example, an audio alarm and a visual alarm may be selected to be activated at the same time. A visual alarm may include turning on one or more lights, for example. In some embodiments, sets of actions may be taken.

For example, a first set of actions may be taken in response to an event. Then, if the user does not solve a cognitive reasoning skills test within a prescribed period of time, a second set of actions may be taken.

In some embodiments, when a user answers the cognitive reasoning skills test incorrectly, another cognitive reasoning skills test is presented that is different from the incorrectly answered cognitive reasoning skills test. In other embodiments, when a user answers the cognitive reasoning skills test incorrectly, the same cognitive reasoning skills test is presented. In some embodiments, when a user answers a cognitive reasoning skills test correctly, all local alarms are turned off, and information is sent to an alarm center 110 indicating that the cognitive reasoning skills test has been passed.

In some embodiments, the user of the glucose monitoring device can specify the order in which the actions are selected and can specify the time given the user to solve a cognitive reasoning skills test before a next action is selected. In some embodiments, the user can select a type of cognitive reasoning skills test, such as, for example, one of an arithmetic problem, a spelling test, a password request, and a fact question. Also, an amount of time given to respond to a first action may be specified to be different from an amount of time given to respond to a second action.

When the action selected by the alarm unit 103 is to send information to the communications network 108, the information may be communicated to a network server/alarm center 110 connected to the communication network 108. The alarm center 110 may be connected to a plurality of alarm units 103 via the communication network 108. The alarm center 110 may include memory and a processor to execute alarm center functions. Alarm center functions may include initiating a contact of a person in response to information received at the alarm center 110. Thus, the alarm center 110 may notify one or more people by telephone 115, by computer 125, by mobile device 135, or other device, via one or more communication networks 112. The communication network(s) 112 may include the communication network(s) 108 or may be a different communications network.

The communications network(s) 108, 112 may include the Public Switched Telephone Network, the Internet, a wireless cellular network, a cable network, a local area network, a wide area network, or any combination thereof.

The information received from the alarm unit 103 via the communications network 108 may include an indication that an event has occurred, the cause of the alarm, the identity, location, and telephone number of the user of the glucose monitoring device 104, blood glucose data, other medical data, the time the event occurred, or any combination thereof.

Notification via the telephone 115, the computer 125, the mobile device 135, or other device may be by telephone call, text message, email, page, instant message, or other method of information delivery. The persons who may be notified include one or more of the user of the glucose monitoring device, a family member of the user, a physician, a caregiver, a significant other of the user, a friend of the user, and an emergency rescuer. For example, in response to the detection of an event, the alarm center 110 may initiate a telephone call to the user at his telephone number. At the same time, the alarm center 110 may initiate a telephone call to a significant other via the telephone 115, send an email to a user of the computer 125, and send a text message to the mobile device 135. If the user of the glucose monitoring device does not solve a cognitive reasoning skills test within a certain period of time, the alarm center 110 may then initiate a call to an emergency rescuer. The person(s) contacted by the alarm center 110 may be selected based on a glucose monitoring device user's individual needs and circumstances. The person(s) to be contacted may be designated by a user of a glucose monitoring device or by his or her guardian or caregiver, for example.

In one illustrative embodiment, the alarm center 110 may be programmed to send a call to a telephone of the glucose monitoring device user 101 to awaken the user by the ring of the phone. The call may be made by a person associated with the alarm center 110, or may be automatically made by an electronic system of the alarm center. The alarm center 110 may be programmed to let the telephone ring for a specified number of rings that may be specified by the user of the glucose monitoring device. A pre-recorded message may be played when the glucose monitoring device user 101 answers the phone. The pre-recorded message may prompt the user to take an action, such as an action that demonstrates the user's cognitive ability to attend to an event. For example, the pre-recorded message may announce to the user that an event has occurred and direct the user to solve a problem, such as an arithmetic problem, displayed on a display of the alarm unit. The solution of the problem may be keyed in by the user using a keypad or touch screen of the alarm unit. The user's ability to solve the problem is indicative of the user's cognitive ability to attend to the event. The problem to be solved may be an arithmetic problem, a spelling test, a password request, a fact question, or any combination thereof. Other cognitive reasoning skills tests can be provided.

FIG. 1 also shows a local computer 145 that may be connected to the alarm unit 103, either directly by wire or wirelessly, or by way of the communications network 108. The local computer 145 may receive data from the glucose monitoring device 104 and from the network server/alarm center 110. The data may include blood glucose level data, and other medical data, including a history of blood glucose level, a log of events detected by the glucose monitoring device, and data including who has been contacted and when and how the contact was made. Information from the glucose monitoring device 104 and the network server/alarm center 110 may be displayed by the local computer 145 as a webpage of the user. The webpage may display information that includes statistical data from the network server/alarm center. The statistical data may include, average glucose level of a plurality of users of the network server/alarm center 110, a number of contacts made for the user 101 over a period of time, average number of contacts made for other users over a period of time, average number of times blood glucose levels of a plurality of user exceeds an upper threshold or falls below a lower threshold, or any combination thereof. Other aggregates of data collected for a plurality of users or the user 101 may also be presented on a webpage displayed by the local computer 145. The functionality for presenting the webpage may reside in the alarm unit 103, the network server/alarm center 110, or the local computer 145.

Figure 2:
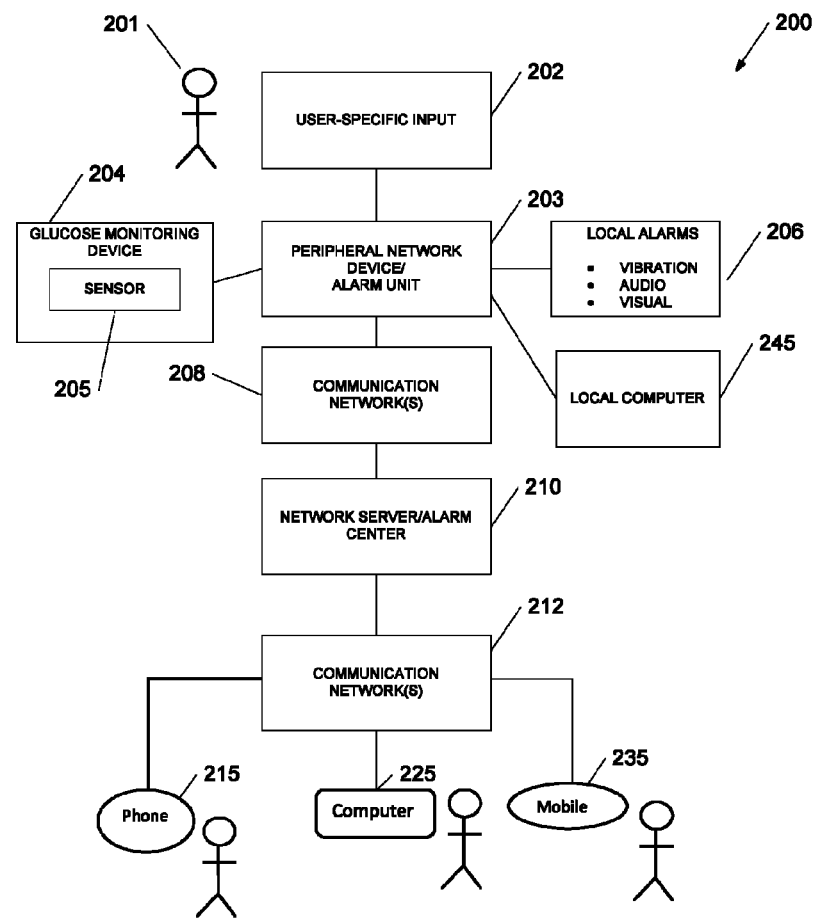
FIG. 2 depicts a second embodiment of a system responsive to an event detected at a glucose monitoring device.

FIG. 2 depicts a second embodiment of a system 200 responsive to an event detected at a glucose monitoring device 204. In the embodiment of FIG. 2, elements corresponding to the like-numbered elements of FIG. 1 may be implemented as described above with reference to FIG. 1. A difference between the embodiment of FIG. 1 and the embodiment of FIG. 2 is the location of the alarm unit. In FIG. 2, the alarm unit 203 is a peripheral network device. The alarm unit 203 may have functionality that is similar to the functionality of the alarm unit 103 of system 100. However, in the system 200, the alarm unit is a device that is separate from the glucose monitoring device 204. The alarm unit 203 may be connected to the communication network 208. In one illustrative embodiment, the alarm unit 203 may receive software downloaded from the communication network 208, giving the alarm unit 203 the alarm unit functionality described herein. Note also, that one or more local alarms 206 may be integrated into the alarm unit 203, in some embodiments. For example, the alarm unit 203 may have a loud speaker. The alarm unit 203 may be connected to the communication network 208 by one or more of a Plain Old Telephone System (POTS) line, an Ethernet cable, a coaxial cable, an optical fiber, a WiFi interface, a wireless cellular interface, or by other wireless or wire line connection. Similarly, the alarm unit 203 may be connected to the local alarms 206 wirelessly or by wire.

A mechanism to connect the glucose monitoring device 204 to the alarm unit 203, either wirelessly or by wire, is provided. In one embodiment, a sensor 205, such as an accelerometer is attached to the glucose monitoring device 204 or is attached to a holster that holds the glucose monitoring device 204. The accelerometer detects when the glucose monitoring device 204 vibrates. A signal from the accelerometer arising from the detection of vibration may be sent to the alarm unit 203. The alarm unit 203 may have functionality to discriminate between vibration arising from an event and vibration or motion arising from a non-event. Frequency discrimination and or temporal discrimination may be employed. In another illustrative embodiment, the sensor 205 is an audio detector that is positioned at the glucose monitoring device 204. The audio detector detects when the glucose monitoring device 204 emits a sound. A signal from the audio detector arising from the detection of the sound may be sent to the alarm unit 203. The alarm unit 203 may have functionality to discriminate between sound arising from an event and sound arising from a non-event. Frequency discrimination and or temporal discrimination may be employed.

In other illustrative embodiments, the glucose monitoring device 204 may have an output port or an antenna to communicate with the alarm unit 203. For example, the glucose monitoring device 204 may have a USB port to receive a USB cable that connects to the alarm unit 203. The USB port may send information to the alarm unit 203. The information may include an indication that an alarm has been detected, the cause of the alarm, a time of the event, blood glucose data, other medical data, battery power data, insulin reservoir level data (in the event that the glucose monitoring device 204 includes an insulin delivery mechanism), or any combination thereof. In another example, the glucose monitoring device 204 may have a Radio Frequency (RF) transceiver to communicate information to the alarm unit 203 wirelessly. The alarm unit 203 may have an RF receiver or transceiver to receive information from the glucose monitoring device 204 wirelessly. Thus, in some embodiments, the alarm unit 203 receives data that is internal to the glucose monitoring device 204.

An advantage of an alarm unit 203 that is separate from the glucose monitoring device 204 is that the display at the separate alarm unit 203 can be made much larger than the display at the glucose monitoring device 204. A larger display enables a larger display of an indication of the cause of the problem, making it easier for the user of the glucose monitoring device to recognize the cause of the problem. The display of the alarm unit 203 may display the cause of the problem, a recommend remedial action to be taken by the user, blood glucose level data, or other information or data received from the glucose monitoring device 204. Also, the display of the alarm unit 203 may display a cognitive reasoning skills test.

In some embodiments, the alarm unit 203 may be embedded in a device that also plays commercial radio stations or has other functionality. For example, alarm unit functionality may be combined with a conventional radio, or may be embedded in a mobile device such as a mobile telephone or laptop computer, or may be embedded in a relatively immobile device such as a desk top or tower computer.

Figure 3:
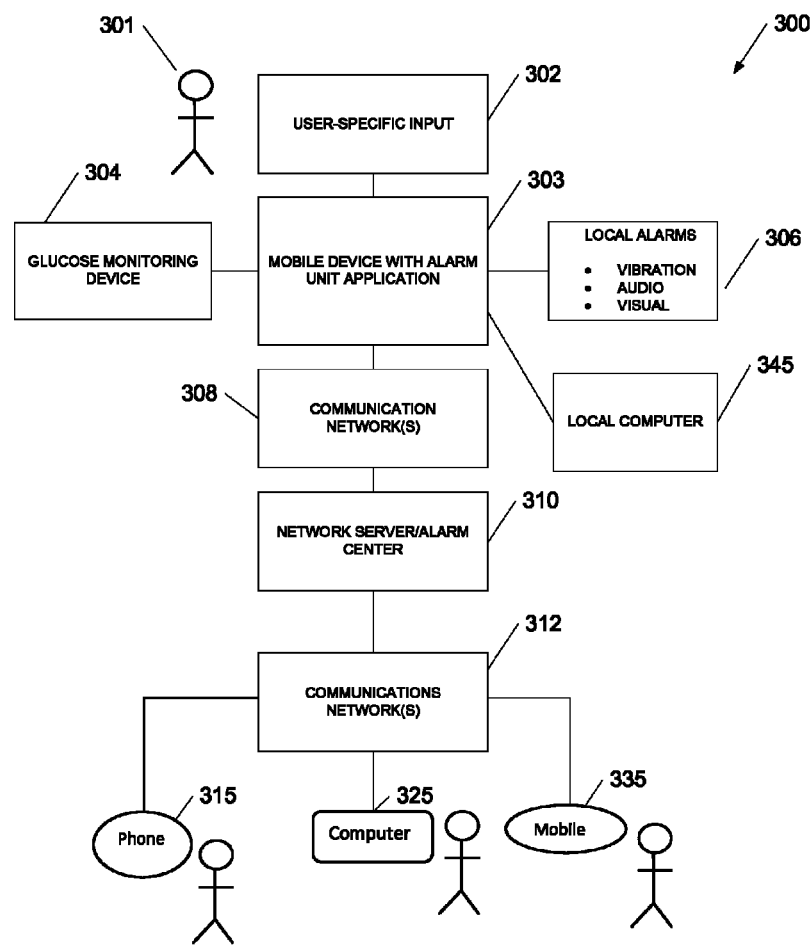
FIG. 3 depicts a third embodiment of a system responsive to an event detected at a glucose monitoring device.

FIG. 3 depicts a third embodiment of a system 300 responsive to an event detected at a glucose monitoring device 304. In the embodiment of FIG. 3, elements corresponding to the like-numbered elements of FIG. 1 may be implemented as described above with reference to FIG. 1. A difference between the embodiment of FIG. 1 and the embodiment of FIG. 3 is the location of the alarm unit functionality described above with reference to FIG. 1. In FIG. 3, the alarm unit functionality is in a mobile device 303, such as a mobile telephone, that includes an alarm unit application. The alarm unit application may be implemented as computer instructions executable by a processor to perform alarm unit functionality.

The glucose monitoring device 304 may be connected to the mobile device 303 wirelessly or by wire. For example, in one illustrative embodiment, the glucose monitoring device 304 is connected to a mobile device docking station to which the mobile device 303 may be docked.

In the embodiment of FIG. 3, the alarm unit functionality of the mobile device 303 may be obtained by downloading alarm unit software from the communication network 308. The alarm unit application of the mobile device 303 may cause the mobile device to display information concerning an event and medical information concerning the user of the glucose monitoring device 304. The alarm unit application of the mobile device may cause the mobile device to "ring" with a distinctive ring tone when an event is detected at the glucose monitoring device 304. The alarm unit application may also cause the mobile device 303 to display a cognitive reasoning skills test and to receive input of an answer to the cognitive reasoning skills test.

Figure 4:
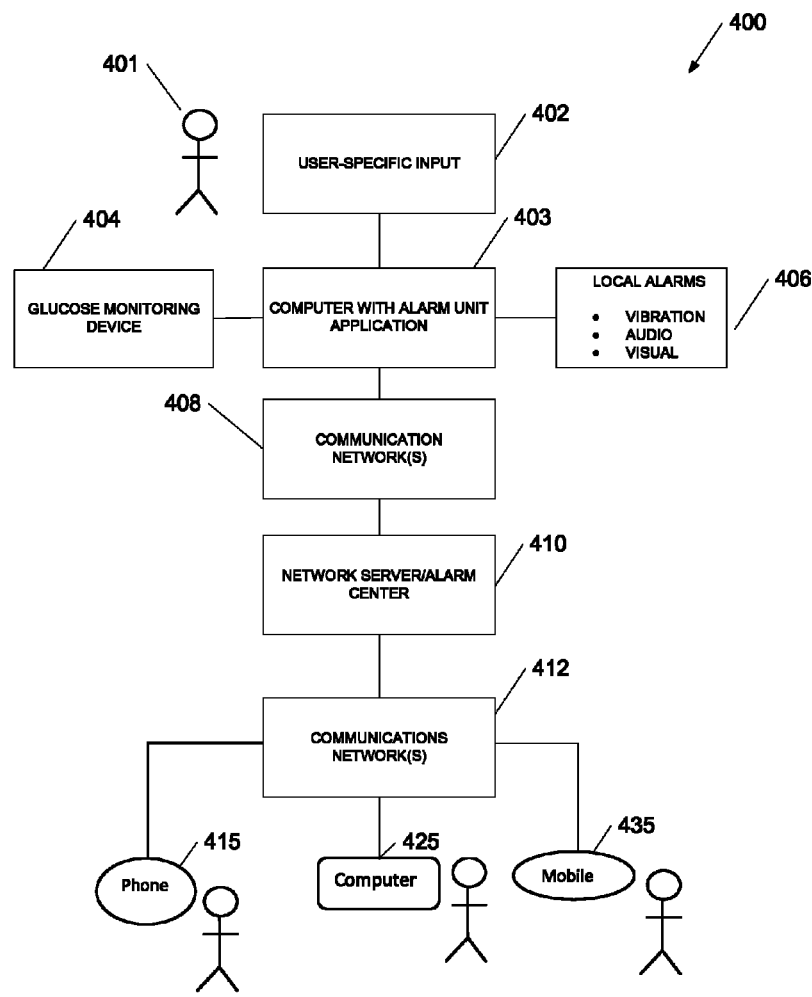
FIG. 4 depicts a fourth embodiment of a system responsive to an event detected at a glucose monitoring device.

FIG. 4 depicts a fourth embodiment of a system 400 responsive to an event detected at a glucose monitoring device 404. In the embodiment of FIG. 4, elements corresponding to the like-numbered elements of FIG. 1 may be implemented as described above with reference to FIG. 1. A difference between the embodiment of FIG. 1 and the embodiment of FIG. 4 is the location of the alarm unit. In FIG. 4, the alarm unit 403 is implemented by a computer. The glucose monitoring device 404 may be connected to the computer 403 wirelessly or by wire. In the embodiment of FIG. 4, the computer 403 may be installed with alarm unit software giving the computer alarm unit functionality as described herein. The alarm unit software may be downloaded from the communication network 408.

In some embodiments, a user may input information to the alarm unit 403. Some or all of this information may be transmitted to the communication network 408 in addition to other information from the alarm unit. Some or all of this information may be transmitted to a third party. For example, the location of the glucose monitoring device user can be transmitted to an emergency rescue unit. The location of the glucose monitoring device user may be entered by the user, or the location can be determined from information received from the communication network 408, or the location can be determined from a GPS receiver. Note also, that the computer with alarm unit 403 may present a webpage of data to the user 401, as described with reference to the computer 145 of FIG. 1.

A computer at the alarm center 410 may display information about the event such as its location and the identification of the user and what type of event triggered the alarm. In some embodiments, internal data of the glucose monitoring device 404 may be transmitted from the glucose monitoring device 404 to the alarm unit 403, and from the alarm unit 403, to the alarm center 410. Access at the alarm center 410 to the information received from the alarm unit 403, may be limited to protect the privacy of the user. For example, in some embodiments, the alarm center 410 may pass a first set of information to a display at the alarm center 410, a second set of information to a second party, and a third set of information to a third party. For example, a display at the alarm center 410 may display an identity, location, and telephone number of the user, and the cause of the alarm, but not display other personal information concerning the user, such as blood glucose level data and medical history information. In contrast the alarm center 410 may send medical history information and blood glucose level data to a physician designated by the user of the glucose monitoring device 404. The features of the system of FIG. 4 may be incorporated into the systems of FIGS. 1-3.

Figure 5:
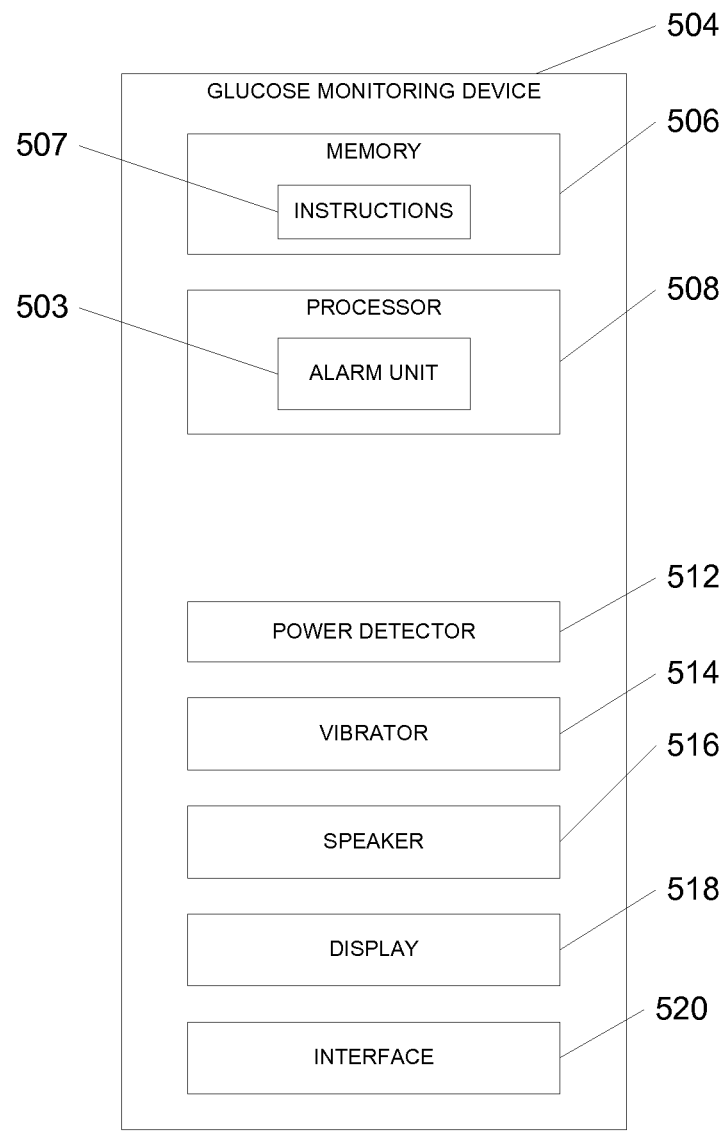
FIG. 5 depicts a glucose monitoring device.

FIG. 5 shows a glucose monitoring device 504 that may have alarm unit 503 functionality, as described above with reference to FIG. 1 and alarm unit 103. The glucose monitoring device 504 includes a memory 506 and a processor 508. The memory 506 stores data and computer instructions 507 to be executed by the processor 508 to perform glucose monitoring device functions. These functions may include monitoring blood glucose level, monitoring rate of change of blood glucose level, monitoring a power level of a battery of the glucose monitoring device 504 via a power detector 512, and other functions. In some embodiments the glucose monitoring device 504 may include an insulin delivery mechanism to provide insulin to a user according to a basal rate computed by the processor 508. In response to an event, a vibrator 514 of the glucose monitoring device 504 may vibrate or a speaker 516 may sound an audio alarm. Also, a display 518 may display information concerning the event. For example, the event may be a large increase in blood glucose level in a short time interval. This information may be displayed on the display 518 in the form of a graph and numerical data.

The glucose monitoring device 504 may also have an interface 520 to enable communication between the glucose monitoring device and another device or a communications network. For example, the interface 520 may include a Universal Serial Bus (USB) connector to receive a USB cable that can be plugged into a network. In another embodiment, the interface 520 includes a wireless transmitter to communicate internal data of the glucose monitoring device 504 to the network, wirelessly. The internal data may include an alarm signal, a glucose level, battery power, insulin reservoir level, basal rate, and other data internal to the glucose monitoring device 504. In embodiments where the alarm unit is located external to the glucose monitoring device, the interface 520 may include an interface to achieve wireless or wire line communication of the internal data to the alarm unit.

Figure 6:
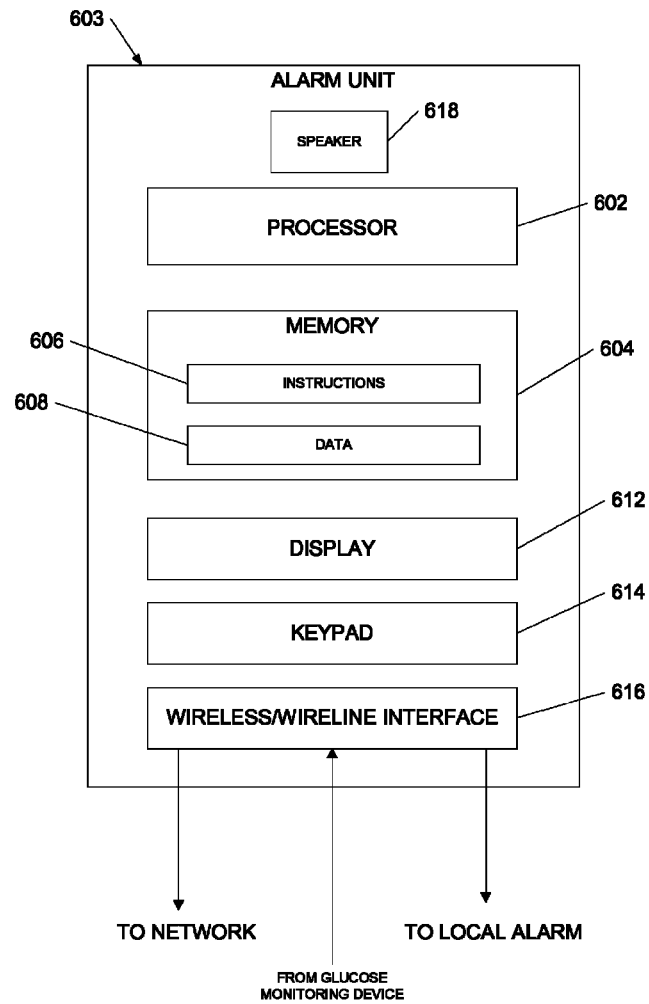
FIG. 6 depicts an illustrative embodiment of an alarm unit to respond to an event at a glucose monitoring device.

FIG. 6 depicts an illustrative embodiment of an alarm unit to respond to an event at a glucose monitoring device The alarm unit 603 includes memory 604 for storing data 608 and computer instructions 606, and a processor 602 for executing the computer instructions 606 to perform alarm functions. For example, the processor 602 may execute computer instructions 606 to implement the alarm unit functionality discussed with reference to FIGS. 1-4. This functionality may include storing alarm options, medical history, information received from a glucose monitoring device, and other data. The functionality may further include selecting alarm options in a specified order, timing, problem generation and display, communicating with a network, determining geographic location, time/date synchronization, and other functionality.

The alarm unit 603 may also include a display 612 and a keypad 614. The display 612 may display information that includes an indication that an event has been detected, the cause of the alarm, a cognitive skills reasoning test, a suggested remedial action, and other information. For example, a user can input a solution to the cognitive skills reasoning test using the keypad 614 or a touch tone screen. In response, the alarm unit 603 may cause display of a suggested remedial action at the display 612. In some embodiments, the display 612 may display information received from the glucose monitoring device. For example, the display 612 may display a graph of blood glucose levels over a period of time.

The display 612 may display information that duplicates information displayed by a display of a glucose monitoring device. However, when the alarm functionality is in a device that is separate from the glucose monitoring device, the display 612 associated with the alarm unit 603 may be substantially larger than the display of the glucose monitoring device and may be better lighted. This enables the user to more quickly and easily determine the cause of the alarm when the cause of the alarm is displayed at the display 612. In some embodiments, the display 612 may display a recommended response to the user. For example, the display 612 may display "Replace Battery" or "Fill Reservoir." The display 612 may also display an indication of whether the alarm unit 603 is connected to a network, and or an indication of whether the alarm unit 603 is in communication with an alarm center.

An embodiment of an alarm unit may also include a wireless and or wire line interface 616 that enables communication between the alarm unit 603 and a communications network, a glucose monitoring device, and one or more local alarms.

Figure 7:
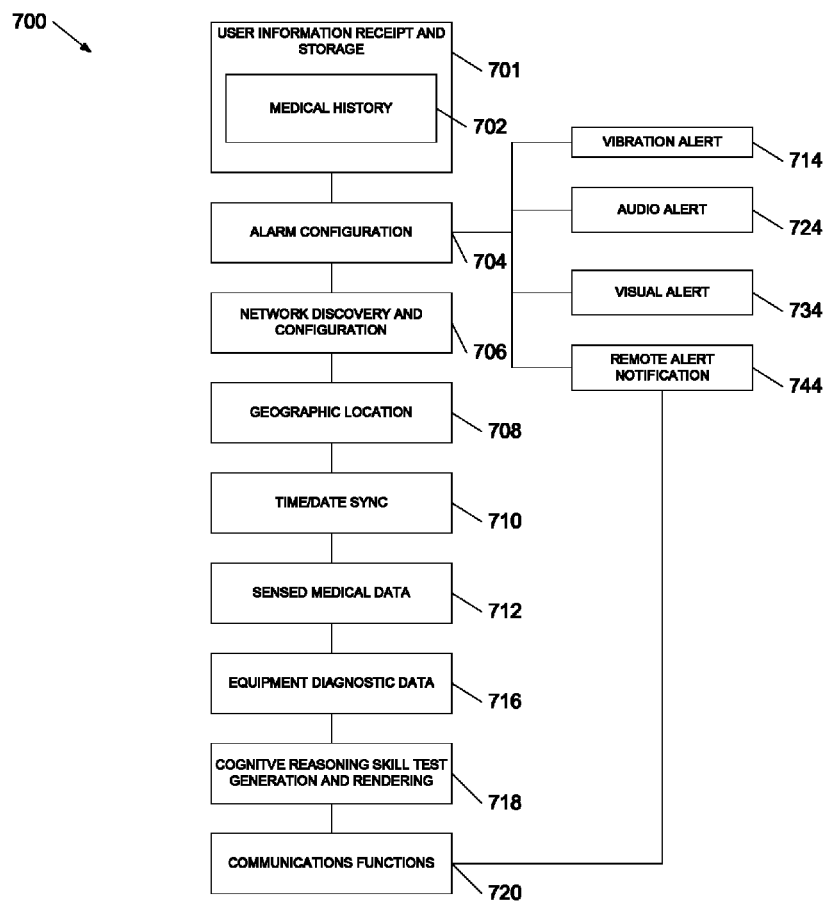
FIG. 7 depicts a diagram illustrating alarm unit functionality in one illustrative embodiment.

FIG. 7 depicts a diagram illustrating alarm unit functionality 700 in one illustrative embodiment. The functionality shown in FIG. 7 may be implemented in the alarm units shown in FIGS. 1-6, and may be realized by application-specific circuitry and or a processor executing computer instructions. The alarm unit may possess functionality to receive information input by a user and to store the information, at 701. Thus, the alarm unit may be responsive to a keypad or touch screen or other mechanism to enable the user to input information to the alarm unit. Such information may include medical history information, at 702. The alarm unit may also store other information that is received from a glucose monitoring device.

The functionality of an alarm unit may include alarm configuration functionality, at 704. The alarm configuration functionality may include functionality to select a vibration alert 714, an audio alert 724, a visual alert 734, and a remote alert notification 744. The alarm configuration functionality may include an ability to select from the available alarms, (which may exceed four), in an order specified by a user of the alarm unit.

The functionality of an alarm unit may include network discovery and configuration functionality, at 706. This functionality includes discovering when a connection to a communications network is available and establishing a communications session with an alarm center server. In one embodiment, a connection between the alarm unit and a network is made when the alarm unit is plugged into a network. In another embodiment, a wireless connection between the alarm unit and a network is automatically made when the alarm unit comes within the vicinity of a wireless access point. As soon as a connection between the alarm unit and a network is made, a handshake may take place between the alarm unit and an alarm center connected to the network to establish a network connection between the alarm unit and the alarm center. This network connection may be established automatically without any action on the part of the user of the alarm unit, other than plugging the device into a network when a wireless connection cannot be made. When a user uses the alarm unit predominantly at his or her residence, a continuous wireless or wire line connection can relatively easily be maintained. Also, a wireless connection may be maintained by way of cell towers in a wireless cellular network. When a user travels, many hotels have wireless or wire line access points in each room, allowing the user to obtain the protection provided by the alarm unit away from home.

The functionality of an alarm unit may include geographic location functionality, at 708. This functionality may include determining a geographic location of the alarm unit, and communicating this information to an alarm center. The geographic location can be input by the user, or may be determined automatically by, for example, associating a geographical location with a network address of the alarm unit. In one illustrative embodiment, geographic location can be obtained from location finding capabilities of a mobile phone in which the alarm unit is embedded. Location finding capabilities may include a Global Positioning System (GPS) receiver.

The functionality of an alarm unit may include time and date synchronization functionality, at 710. This functionality may include determining from a communications network, accurate time and date information and storing time and date information in a memory of the alarm unit or a memory associated with the alarm unit. Other information may be received from the network. For example, an alarm center, such as the alarm center 210 of FIG. 2, may send to the alarm unit 203 the names of persons or entities that were contacted by the alarm center 210 in response to information from the alarm unit 203. The functionality of an alarm unit may include storing sensed medical data, such as blood glucose level data, at 712. The functionality of an alarm unit may also include performing equipment diagnostic tests, and storing and displaying equipment diagnostic data, at 716.

The functionality of an alarm unit may include generating and rendering a cognitive reasoning skills test, at 718. Such a test may include an arithmetic test, a spelling test, a pass code request, a fact question, or other test. The functionality may include receiving input from a keypad, touch screen, or other input technology, in response to a prompt to enter a response to the cognitive reasoning skills test. The functionality of an alarm unit may include communications functionality, at 720. The communications functionality may include functionality to establish a network connection and facilitate communication of information between the alarm unit and the network.

Figure 8:
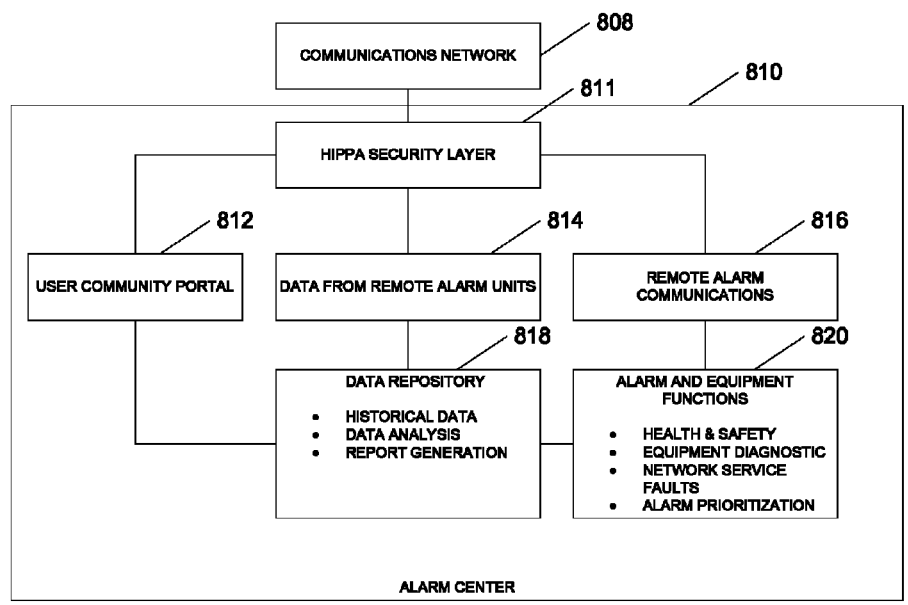
FIG. 8 depicts a diagram illustrating alarm center functionality in one illustrative embodiment.

FIG. 8 depicts a diagram illustrating alarm center functionality 810 in one illustrative embodiment. In one illustrative embodiment, a Health Insurance Portability and Accountability Act (HIPPA) security layer 811 is provided. The HIPPA security layer ensures that information received by the alarm center 810 is handled in accordance with the privacy provisions of the HIPPA and other applicable law. In some embodiments, information received from the communication network 808 may be categorized as information that may be disclosed to a person at the alarm center and information that may not be disclosed to a person at the alarm center. The information received from the communication network 808 may be categorized as information that may be transmitted to a third party and information that may not be transmitted to a third party. Therefore, in one embodiment, access to information received and stored at the alarm center is controlled.

The alarm center functionality of FIG. 8 may include a user community portal 812. The user community portal enables access to community information, user information, and equipment information. Alarm center functionality may include receiving data from remote alarm units 814 and storing the data in a data repository 818. The data repository 818 may store historical data, perform data analysis, and generate reports. Alarm center functionality may include remote alarm communications 816. Remote alarm communications 816 includes receiving alarm information, initiating contact with the user and or one or more third parties according to prescribed rules, and sending alarm information to the user or third parties.

Alarm center functionality may include alarm and equipment functions 820. The alarm and equipment functions 820 may include classifying an alarm as one of a health and safety alarm or an equipment alarm. A health and safety alarm may include a low blood glucose alarm. An equipment alarm may include a low power alarm. The alarm center 810 may take one set of actions if the alarm is a health and safety alarm and may take another set of actions if the alarm is an equipment alarm. For example, the alarm center 810 may contact a medical caregiver in the event of a health and safety alarm, and may contact only the user in the event of an equipment alarm. The alarm and equipment functions 820 may include evaluating equipment diagnostic data and network service faults. In an event of receiving multiple alarms, the alarm and equipment functions 820 may prioritize alarms for response. For examples, older alarms may receive higher priority than newer alarms. As another example, a blood glucose level event may receive higher priority than a low battery event.

Figure 9:
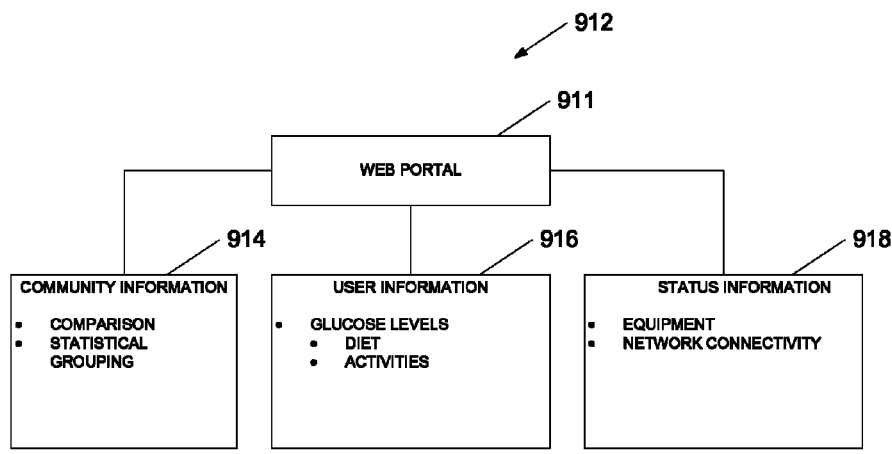
FIG. 9 depicts a diagram illustrating an illustrative embodiment of a user community portal.

FIG. 9 depicts a diagram illustrating an illustrative embodiment of a user community portal 912, such as the user community portal 812 of FIG. 8. The user community portal 912 may include a web portal 911 that includes a web page with links and buttons that may be selected to access information via the web portal. The user community portal 912 may include a community information database 914. The community information database 914 may include comparisons of a user's sensed medical data to the average sensed medical data of the other users. The user can learn from the community information database where she or he ranks among other users with respect to an item of information. For example, a user may determine where she or he ranks in terms of a number of events occurring in a time interval. A user may learn where she or he ranks in terms of a number of events of a particular type occurring in a time interval. Other statistical comparisons can be made. Data of the user community portal may be displayed by the local computer 145 of FIG. 1, the local computer 245 of FIG. 2, the local computer 345 of FIG. 3, or the computer 403 of FIG. 4.

The web portal 911 may give access to information in a user information database 916. Access to the user information database 916 may require a password. The user information database 916 may provide information such as a user's glucose level as a function of diet and activities, and as a function of time. Other user information may be compiled and displayed. The web portal 911 may give access to status information 918, such as equipment status and network connection status.

Figure 10:
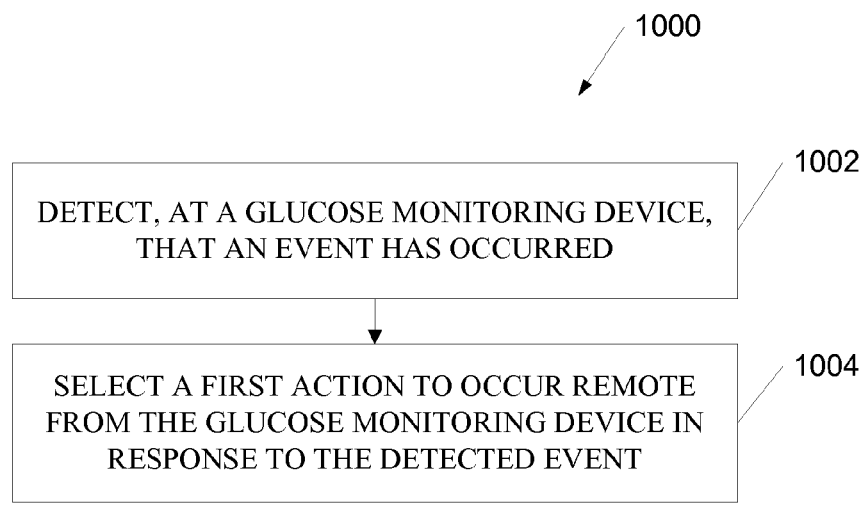
FIG. 10 depicts a flow diagram of a first embodiment of a method of responding to an event detected at a glucose monitoring device.

FIG. 10 depicts a flow diagram 1000 of a first embodiment of a method of responding to an event detected at a glucose monitoring device. An alarm unit, such as the alarm unit 103 of FIG. 1, detects that an event has occurred at a glucose monitoring device, at 1002. The event may be, for example, detection that a low blood glucose condition exists. The alarm unit selects a first action to occur remote from the glucose monitoring device in response to the detected event, at 1004.

Figure 11:
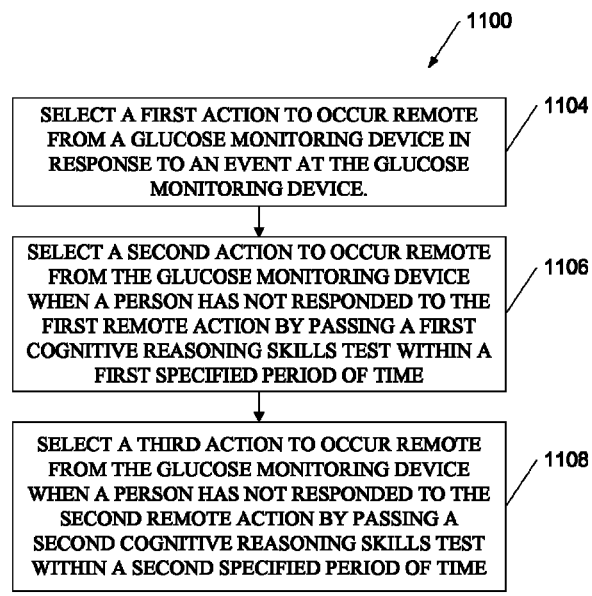
FIG. 11 depicts a flow diagram of a second embodiment of a method of responding to an event detected at a glucose monitoring device.

FIG. 11 depicts a flow diagram 1100 of a second embodiment of a method of responding to an event detected at a glucose monitoring device. A first action is selected to occur remote from a glucose monitoring device in response to an event at the glucose monitoring device, at 1104. A second action is selected to occur remote from the glucose monitoring device when a person has not responded to the first remote action by passing a first cognitive reasoning skill test within a first specified period of time, at 1106. A third action is selected to occur remote from the glucose monitoring device when a person has not responded to the second remote action by passing a second cognitive reasoning skill test within a second specified period of time, at 1108. The first and second cognitive reasoning skills tests may be the same. The first and second specified periods of time may be equal. Also, as previously noted, more than one action can be taken at the same time.

Figure 12:
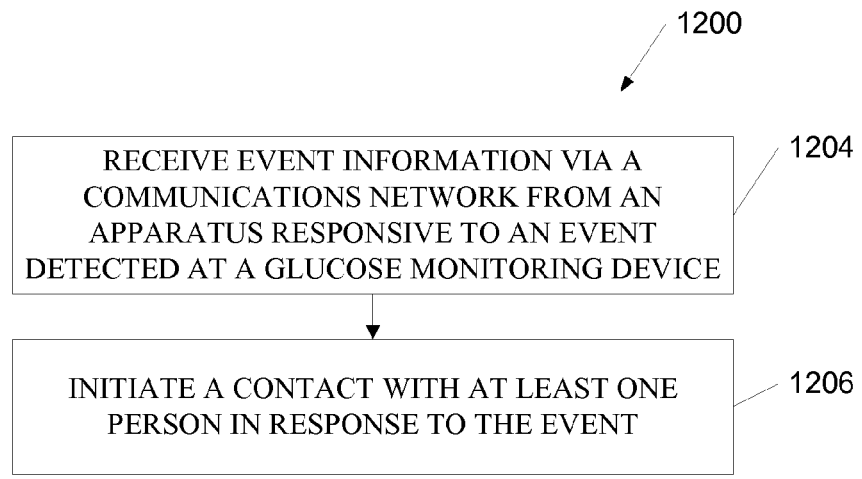
FIG. 12 depicts a flow diagram of a third embodiment of a method of responding to an event at a glucose monitoring device.

FIG. 12 depicts a flow diagram 1200 of a third embodiment of a method of responding to an event at a glucose monitoring device. Event information is received via a communications network from an alarm unit responsive to an event detected at a glucose monitoring device. In response to the event, a contact with at least one person is initiated.

Another illustrative embodiment includes a machine-readable medium embodying machine-readable instructions that, when executed by a processor, cause the processor to select an action to occur remote to a glucose monitoring device in response to an event detected at the glucose monitoring device. For example, a local alarm may be activated in response to an event. As another example, a person may be contacted in response to an event. The processor-readable medium may include a compact disk, a flexible disk, a digital video disk, a hard drive, solid state memory, magnetic memory, electronic memory, optical memory, or other tangible memory.

Various changes, substitutions and alterations can be made to the embodiments described herein without departing from the scope of the appended claims. An embodiment may achieve multiple objectives, but not every embodiment falling within the scope of the attached claims will achieve every objective. Moreover, the scope of the present application is not intended to be limited to the particular embodiments of the process, machine, manufacture, composition of matter, means, methods and steps described in the specification. One of ordinary skill in the art will readily appreciate from this disclosure that processes, machines, manufacture, compositions of matter, means, methods, or steps, presently existing or later to be developed are equivalent to, and fall within the scope of what is claimed. Accordingly, the appended claims are intended to include within their scope such processes, machines, manufacture, compositions of matter, means, methods, or steps.

What is claimed is:

1. An apparatus, comprising:
   an external sensor external to and positioned at a glucose monitor, the sensor generating a signal indicating an alarm condition detected by the glucose monitor, the sensor being an accelerometer detecting when the glucose monitor vibrates to indicate an alarm condition detected by the glucose monitor, the accelerometer further generating the sensor signal in response to detecting the vibration;
   an alarm device responsive to the sensor signal to activate a first manifestation of an alarm, a type of the first manifestation of the alarm being at least one of a vibration, a sound, a visual manifestation, and an electronic communication, the alarm device automatically presenting a first cognitive reasoning skills test without third party intervention to a user of the glucose monitor in response to detecting the alarm condition.

2. The apparatus of claim 1, wherein the alarm device ceases the first manifestation of the alarm upon a user passing the first cognitive reasoning skills test.

3. The apparatus of claim 1, wherein the alarm device presents a second cognitive reasoning skills test upon a user failing the first cognitive reasoning skills test.

4. The apparatus of claim 1, wherein the first manifestation of the alarm is a first type, and a second manifestation of the alarm is a second type different from the first type, the second manifestation of the alarm being activated upon a user failing the first cognitive reasoning skills test.

5. The apparatus of claim 1, wherein the cognitive reasoning skills test is selected at random.

6. The apparatus of claim 1, wherein the alarm device is programmable by a user to select one of an order of cognitive reasoning skills test types to be presented, and an order of alarm types to be presented.

7. The apparatus of claim 1, wherein an alarm condition includes at least one of a low battery, a low insulin level of an insulin pump, a malfunction of the glucose monitor, and a malfunction of an insulin pump.

8. A method, comprising:
  detecting a first alarm emanating from a glucose monitoring device, the detecting via a sensor positioned at the glucose monitoring device, the sensor producing a sensor signal in response to detecting the first alarm, the first alarm indicative of one of an adverse glucose level and an adverse glucose rate of change;
  receiving the sensor signal at a device remote from the glucose monitoring device, the remote device emitting a second alarm in response to the sensor signal;
  automatically presenting a first cognitive reasoning skills test in response to the sensor signal without third party intervention; and
  automatically presenting a second cognitive reasoning skills test upon a user failing the first cognitive reasoning skills test.

9. The method of claim 8, wherein the sensor is external to the glucose monitoring device.

10. The method of claim 8, further comprising receiving input from a user in response to the presenting of the cognitive reasoning skills test and automatically determining if the input satisfies the cognitive reasoning skills test without third party intervention.

11. The method of claim 10, further comprising emitting from the remote device a third alarm different from the second alarm when the input fails to satisfy the cognitive reasoning skills test.

12. The method of claim 10, wherein the second alarm is an adjustable sound substantially louder than a sound made by the glucose monitoring device.

13. The method of claim 10, wherein the second alarm is a vibration substantially stronger than a vibration made by the glucose monitoring device.

14. A non-transitory machine-readable medium embodying machine-readable instructions that, when executed by a processor, cause the processor to perform functions that include:
  emitting a second alarm signal in response to a first alarm signal detected by a sensor positioned at and removable from a glucose monitoring device; and
  automatically presenting a first cognitive reasoning skills test without human intervention in response to the first alarm signal; and
  automatically evaluating a response of a user of the glucose monitoring device to the first cognitive reasoning skills test without third party intervention; and
  wherein the second alarm signal is an adjustable sound substantially louder than a sound made by the glucose monitoring device.

15. The non-transitory machine-readable medium of claim 14, wherein the functions further include automatically presenting a second cognitive reasoning skills test without third party intervention in response to a user inputting a response that fails the first cognitive reasoning skills test.

16. An apparatus, comprising:
  an external sensor external to and removably affixable to a glucose monitoring device, the sensor responsive, when positioned externally at the glucose monitoring device, to a first alarm emitted by the glucose monitoring device to produce a sensor signal, the first alarm indicative of one of an adverse glucose level and an adverse glucose rate of change; and
  a secondary alarm device positionable remote to the glucose monitoring device and responsive to the sensor signal, the secondary alarm device emitting a second alarm, the secondary alarm device automatically presenting a first cognitive reasoning skills test to a user of the glucose monitor in response to detecting the alarm condition and automatically terminating the second alarm if the user passes the first cognitive reasoning skills test, and upon the user failing the first cognitive reasoning skills test, the secondary alarm device emitting a third alarm different in type from the second alarm.

* * * * *